(12) United States Patent
Khanuja et al.

(10) Patent No.: US 6,455,079 B1
(45) Date of Patent: Sep. 24, 2002

(54) **PROCESS OF ITS APPLICATION AGAINST LEPIDOPTERAN INSECTS USING *ALBIZZIA LEBBECK* PLANT EXTRACT AND *BACILUS THURIENGIENSIS* DELTA-ENDOTOXIN**

(75) Inventors: Suman Preet Singh Khanuja; Sarita Satapathy; Subhash Chandra Singh; Tiruppadiripuliyur Ranganathan Santha Kumar; Jai Shankar Arya; Arun Kumar Tripathy; Ajit Kumar Shasany; Mahendra Pandurang Darokar; Sushil Kumar, all of Lucknow (IN)

(73) Assignee: Council of Scientific and Industrial Research, New Dehli (IN)

( * ) Notice: Subject to any disclaimer, the term of this patent is extended or adjusted under 35 U.S.C. 154(b) by 0 days.

(21) Appl. No.: 09/923,586

(22) Filed: Aug. 7, 2001

Related U.S. Application Data

(63) Continuation of application No. 09/541,357, filed on Mar. 31, 2000, now abandoned.

(51) Int. Cl.$^7$ .................. A61K 35/38; A61K 35/00; A01N 25/00

(52) U.S. Cl. .................. 424/725; 424/780; 424/405; 514/2

(58) Field of Search .................. 424/725, 780, 424/405; 514/2

(56) References Cited

U.S. PATENT DOCUMENTS 4,935,353 A * 6/1990 Burges et al.
5,446,019 A * 8/1995 Ely et al.
5,501,852 A * 3/1996 Meadows et al.

OTHER PUBLICATIONS

Ayoub et al. Intl. J. Crude Drug Res. 1986. vol. 24, No. 1, pp. 16–18.*

* cited by examiner

*Primary Examiner*—Christopher R. Tate
(74) *Attorney, Agent, or Firm*—Fish & Richardson P.C.

(57) ABSTRACT

The present invention provides a novel synergistic composition comprising extract obtained from the plant *Albizzia lebbeck* together with *Bacillus thuringiensis* δ-endotoxin, useful in controlling lepidopteran insects, methods for the preparation of the composition and application of the insecticidal composition to standing crops.

14 Claims, No Drawings

PROCESS OF ITS APPLICATION AGAINST LEPIDOPTERAN INSECTS USING *ALBIZZIA LEBBECK* PLANT EXTRACT AND *BACILUS THURIENGIENSIS* DELTA-ENDOTOXIN

RELATED APPLICATION

This application is a continuation of U.S. Ser. No. 09/541,357, filed Mar. 31, 2000, now abandoned.

FIELD OF THE INVENTION

The present invention relates to a novel insecticidal composition comprising extract(s) obtained from the plant *Albizzia lebbeck* and δ-endotoxin from *Bacillus thuringiensis*, useful in effectively controlling the lepidopteran crop damages insects. The invention also provides a process for the preparation of the said composition and a method for the application of the composition.

BACKGROUND OF THE INVENTION

Insecticides have long been used against harmful insects, pests in plants. Insects of the order 'Lepidoptera' particularly cause maximum damage to the field crops, drastically reducing the economic yield of cultivated plants. Globally, the estimates put crop loss due to insect attack somewhere between 18 to 30%. The pesticides and repellents available in the prior art, however, suffer from various deficiencies. Often, compositions provided are insect repellents and not insecticidal. Furthermore, many compositions are either toxic or generally unpleasant to the human beings and animals. Still others require complicated process to provide active ingredients for efficient protection.

Many synthetic prior art compositions have been proposed as insect repellents, but have later been determined to be unsuitable for safe use by humans, as these are not selective and cause grave concern by damaging the environment. Moreover, the use of repellents is not feasible practically for agricultural use.

Various crude extracts and essential oils from plants, such as Neem extract and compounds from *Azadirachta indica*, citronella oil obtained from Cymbopogon species, or eucalyptus oil obtained from Eucalyptus species etc., have been reported to be useful in insect pest management but mostly as pest repellents. These also suffer from limited activity, unpleasant odor, inconsistency and unreliable composition. Most of the art for plant based insecticide formulation deals with complex compositions with several ingredients required in heavy dosages. The need of the hour is effective insecticidal composition, which is easier to consistently produce and monitor. In the art there are many examples of production and application of different preparations from *Bacillus thuringiensis* δ-endotoxin for plant protection. but the apprehension is of the resistance development in the insect population due to continuous monotonous exposure of this toxin to the insects. Therefore, the applicants studied the combination of microbial pesticides with botanical insecticidal compounds and found that the formulation consisting of diverse compounds with novel and different modes of action is capable of reducing the risk and probability of simultaneous resistance development.

Accordingly, the applicants have developed a plant based insecticidal composition which when combined with other biological insecticide(s) including *Bacillus thuringiensis* δ-endotoxin restricts resistance development against the endotoxin. Further, the composition is environmentally safe and economically effective with significantly lower dosage.

OBJECTS OF THE INVENTION

The main object of the invention is to provide a novel insecticidal composition comprising alcoholic extract obtained from the plant *Albizzia lebbeck* together with *Bacillus thuringiensis* δ-endotoxin.

Yet another object of the invention is to provide an insecticidal combination that is effective at very low dosage against plant pests, such as lepidopteran insects.

Another object of the invention is to provide a composition that may be used for these insects as spray.

Still another object is to provide a composition that exhibits synergistic properties and is capable of enhancing the effect of the endotoxin and killing the resistance developed by insects due to sole application of δ-endotoxin.

Another object is to provide process for the preparation of the novel insecticidal composition of the invention.

Yet another object of the invention is to provide a method of application of the composition in terms of sequence of repeat treatments effective in controlling insect population below the threshold level of economic damage.

SUMMARY OF THE INVENTION

The present invention provides a novel synergistic composition comprising alcoholic extract obtained from the plant *Albizzia lebbeck* together with *Bacillus thuringiensis* δ-endotoxin acetone powder. The compositions can be sprayed on the infested standing crops. The said composition exhibits potency at very low dosage against lepidopteran insects. The invention also describes a method for the preparation and application of the insecticidal composition.

DETAILED DESCRIPTION OF THE INVENTION

The composition and the method of application as described in the present invention is intended to be used against all plant pests, which succumb to the lethal properties of the two biocontrol agents and their synergistic combination thereof.

The invention provides novel insecticidal composition comprising alcoholic extract obtained from the plant *Albizzia lebbeck* together with *Bacillus thuringiensis* δ-endotoxin useful in controlling insects of the class lepidoptara.

In an embodiment the composition is useful in controlling insects selected from the class lepidoptara comprising *Spilarctia obliqua*, *Spodoptera litura* and *Heliothis armigera*.

Yet another embodiment the concentration of the plant extract in the composition is about 2.5 mg/ml alcohol for killing insects.

In another embodiment the δ-endotoxin obtained from *Bacillus thirungiensis* is obtained as acetone powder.

In still another embodiment the alcoholic extract is used in combination with *Bacillus thuringiensis* δ-endotoxin at a concentration of about LC 5 or more of both the constituents.

One more embodiment relates to a process for the preparation of the insecticidal composition, said process comprising the steps of collecting, drying, pulverizing part of the plant *Albizzia lebbeck*, treating the pulverized plant parts with alcohol, filtering and evaporating the alcohol, drying in a freeze drier, and dispersing the alcoholic extract in *Bacillus thuringiensis* δ-endotoxin acetone powder.

In an embodiment the plant parts used for preparation of extract are selected from stem, leaves or seeds.

Yet another embodiment the alcohol is selected from Ethanol, Methanol and Isopropanol.

Still another embodiment the pulverized plant parts are kept in about 100 ml to 5 litre alcohol per 100 gram of plant material overnight for 7 days at room temperature.

In an embodiment the alcohol is filtered out using Whatman no.1 filter paper and evaporated naturally or in a rotavapour at 40–60° C.

Yet another embodiment the extract is dried in a freeze drier at −110° C.

Still another embodiment the insecticidal composition is capable of controlling in insects selected from the class Lepidoptera comprising *Spilarctia obliqua, Spodoptera litura* and *Heliothis armigera.* vent or can be combined with any other insecticidal preparations like *Bacillus thuringiensis* δ-endotoxin.

Insecticidal Bioassay

These preparations were dissolved in ethanol or water and coated on castor (*Ricinus communis*) leaf in a series of concentrations mentioned in Table 1. In case of ethanol the coated leaf was dried at ambient temperature such that the leaf did not lose its freshness and fed to 6 to 10 days old larvae of *Spilarctia obliqua* in petriplates. The experiments were conducted in replicated trial by taking 30 larvae per treatment with 5 replications. The treated plant materials were changed every second day. The larvae were observed for growth and feeding behavior everyday and % mortality was noted on $9^{th}$ day of the experiment.

TABLE 1

Percentage larval mortality (after 9 days) upon feeding different concentrations of the extract*.

| Extract from | Control: No coating | Control: coated with solvent | Concentration of the extract in μl ethanol: 1.0 | 0.5 | 0.25 | 0.125 | 0.0625 | 0.0312 | 0.0165 | 0.0082 |
|---|---|---|---|---|---|---|---|---|---|---|
| Stem | 0 | 0 | 100 | 100 | 100 | 100 | 100 | 100 | 50 | 25 |
| Leaf | 0 | 0 | 100 | 100 | 100 | 100 | 50 | 20 | 10 | 5 |
| Seed | 0 | 0 | 100 | 100 | 100 | 100 | 100 | 50 | 25 | 10 |

*400 μl of given concentration of treatment was coated on leaf of 12 square centimeter.

In an embodiment the concentration of the plant extract is about 2.5 mg/ml and the concentration of δ-endotoxin is about LC 5 or more of both the constituents.

One more embodiment a method of application of the insecticidal composition said method comprising the step of spraying the insecticidal composition on standing crops.

The Present Invention in its Disclosure Provides the Process for the Preparation of the Extract from the Plant The processing of plant parts to obtain usable extract as biocontrol agent can be achieved in the following sequence of steps:

Step 1: The plant material (leaf stem and seed) are collected/harvested from the plant preferably in the month of Step 2: The material is shade dried carefully by regular respreading in a clean environment such that no microbial infestation occur.

Step 3: Percolation: An alcohol, preferably ethanol sufficient to dip the plant material (1.0 to 5.0 liter per kilogram of plant material) 1 is added to the plant material in a percolator and kept overnight to 7 days at room temperature.

Step 4: Alcohol part is filtered out by Whatman no.1 filter paper and evaporated naturally or in a rotavapour at 40–60° C. The leftover plant material is reprocessed with fresh alcohol in similar fashion.

Step 5: Then these extracts are pooled.

Step 6: Further drying of the pooled extract is performed in a freeze drier at −100° C. (optional).

Step 7: The final extract thus obtained can be powdered and used for spraying after dissolving in suitable sol- From the above table it was observed that the extract from stem was more potent as larvicidal because it kills 50% of the insects at a concentration of 0.0165 μg/μl compared to the extract from leaf (0.0625 μg/μl) and seed (0.0312 μg/μl). LC50 was estimated as the concentration at which 50% mortality of the larvae was observed and similarly the other lethal doses were determined.

Lifecycle Disruption Assays

In the next step we studied the effect of the extract on pupation, adult emergence and hatching of eggs upon continuously feeding the larvae on non-lethal or sub-lethal doses of the extracts. The results obtained were interesting and as described in Table 2. In this experiment 0.0312 μg/μl concentration of the extracts was found effective.

TABLE 2

Lifecycle disruption in *Spilarctia obliqua* by the extract of *Albizzia lebbeck* at sub-lethal concentration (0.0312 μg/μl)

| Activity | Extract from stem | Extract from leaf | Extract from seed | Control solvent | Control water |
|---|---|---|---|---|---|
| Larvicidal | 100 | 100 | 100 | 0 | 0 |
| Pupicidal | 80 | 80 | 70 | 0 | 0 |
| Adult | Eggs did not hatch | Eggs hatched | Eggs did not hatch | Eggs hatched | Eggs hatched |

So it was evident from the above experiment that the extract front stem was more potent than leaf and seed and disrupts the lifecycle of the insect at every stages of the lifecycle.

Defining LC Values for Bt Acetone Powder

In the next step we carried out feeding the larvae with different concentrations of *Bacillus thuringiensis* δ-endotoxin protein preparation in form of acetone powder which was prepared in the following manner. *Bacillus thuringiensis* cells were grown in MGM broth for 62 h. the pH of the culture was brought down to 7.0 using 1 N HCl. Cells were pelleted by centrifugation at 8000rpm for 20 min. Cell pellet was suspended in 6% lactose (0.1–0.2 volume) by stirring for 30 min. on magnetic stirrer and acetone (4 volumes) was added slowly while stirring which was continued for another 30 min. Suspension was allowed to stand for 10 min. and th4en filtered through filter paper (Whatman no. 1) under suction. Residue was resuspended in 25 ml of acetone and stirred for 30 min. This process was repeated three times. Finally residue was dried overnight in a vacuum desicator at 25° C. This residue (also called acetone powder) contained the crude ednotoxin. Mortality observed for the larvae on $9^{th}$ day of treatment is given in Table 3.

TABLE 3

Percent larval mortality on $9^{th}$ day in *Spilarctia obliqua* against Bt acetone powder.

| Concentrations of Acetone powder | Control | 400 μg/ 400 μl | 200 μg/ 400 μl | 100 μg/ 400 μl | 40 μg/ 400 μl | 25 μg/ 400 μl |
|---|---|---|---|---|---|---|
| Percent mortality | Nil | 70 | 65 | 45 | 20 | 10 |

From this experiment the LC10 and LC50 values were calculated as 25 μg/400 μl and 125 μg/400 μl respectively by plotting a standard curve of Acetone Powder Vs. Mortality.

Development of Synergistic Combination

To check whether the plant extract has an enhancing effect on the δ-endotoxin we fed the larvae with different concentrations of the stem extract and the endotoxin (Table 4).

TABLE 4

Activity of the extract and δ-endotoxin in combination.

| % Effect | LC 10 42 | LC 10 E | LC5 B + LC5 E | LC25 B | LC25 E | LC 12.5 B - +LC 12.5 E | LC50 B | LC50 E | LC25 B - LC25 E | Control | Control coated solvent |
|---|---|---|---|---|---|---|---|---|---|---|---|
| Larvicidal | 10 | 10 | 10 | 26 | 25 | 62 | 45–50 | 45–55 | 66–75 | 0 | 0 |
| Pupicidal | 20 | 20 | 50 | 52 | 50 | 60 | 55 | 48 | 70 | 0 | 0 |
| Hatching | 0 | 33 | 0 | 0 | 0 | 0 | 0 | 0 | 0 | 100 | 100 |

As described in the table the pupicidal activity increases significantly to 20%. in the combination at a dose of LC 5 each, in comparison to, when applied separately at a concentration of LC 10. Similarly for the larvicidal and pupicidal activity at a concentration of LC 12.5 and LC 25 in the combinations, is much higher than LC 25 and LC 50 when taken individually. So the conclusion was that, the plant extract and *Bacillus thuringiensis* δ-endotoxin have synergistic effect enhancing the effectiveness of one another. Even the larvae escape mortality after feeding on the combination, the adult may not emerge from the pupae or the eggs will not hatch. This combination is environmentally safe as tested earlier for δ-endotoxin. The plant also produces many compounds, which are used for medication for human.

We started our study keeping in view the Lepidopteran insect *Spilarctia obliqua* which cause wide spread damage to Mentha species. This is an insect of first magnitude with world wide in distribution. It is polyphagous and major pest of several crops like radish, soybean, groundnut, blackgram, bengalgram, cowpea, sunflower, cabbage, rye, jute, mint, turmeric, cotton, in India. But after observing the effect we were encouraged to test the effect on other lepidopteran plant insects like *Spodoptera litura* and *Heliothis armigera* with similar results. So the present invention provides insecticidal compositions comprising a plant extract in alcohol, as applied as a lone insecticide or the plant extract with *Bacillus thuringiensis* δ-endotoxin as a combination insecticide with synergistic effect. The composition of plant extract and *Bacillus thuringiensis* δ-endotoxin can be prepared in alcohol at required concentrations. properly dispersed and sprayed on the infested plants. These combinations as described in the tables were tested on the plants of *Mentha arvensis* infested with *Spilarctia obliqua* in the glasshouse and in the field with complete dis-infestation within 15 days.

What is claimed is:

1. An insecticidal composition comprising:
   (a) alcoholic extract obtained from one or more parts of the plant *Albizzia lebbeck;* together with
   (b) *Bacillus thuringiensis* δ-endotoxin, useful in controlling insects of the class lepidoptara,
   ingredients (a) and (b) together being present in amounts that, taken together, are insecticidally effective.

2. A composition as claimed in claim 1 wherein the composition is useful in controlling insects selected from the class lepidoptara comprising *Spilarctia obliqua, Spodoptera litura* and *Heliothis armigera*.

3. A composition as claimed in claim 1 wherein the concentration of the plant extract in the composition is about 2.5 mg/ml alcohol for killing insects.

4. A composition as claimed in claim 1 wherein the alcoholic extract is used in combination with *Bacillus thuringiensis* δ-endotoxin at a concentration of about LC 5 or more of both the constituents.

5. A composition as claimed in claim 1 wherein δ-endotoxin from *Bacillus thuringiensis* is used as acetone powder.

6. A process for the preparation of an insecticidal composition as claimed in claim 1, said process comprising the steps of collecting, drying, pulverizing one or more parts of the plant *Albizzia lebbeck*, treating the one or more pulverized plant parts with alcohol, filtering and evaporating the alcohol, drying in a freeze drier, and dispersing the alcoholic extract in *Bacillus thuringiensis* δ-endotoxin acetone powder.

7. A process as claimed in claim 5 wherein the plant parts used for preparation of extract are selected from stem, leaves or seeds.

8. A process as claimed in claim 5 wherein the alcohol is selected from ethanol, methanol and isopropanol.

9. A process as claimed in claim 5 wherein the pulverized plant parts are kept in about 100 ml to 5 litre alcohol per 100 gram of plant material overnight for 7 days at room temperature.

10. A process as claimed in claim 5 wherein the alcohol is filtered out using Whatman no.1 filter paper and evaporated naturally or in a rotavapour at 40–60° C.

11. A process as claimed in claim 5 wherein the extract is dried in a freeze drier at −110° C.

12. A process as claimed in claim 5 wherein the insecticidal composition is capable of controlling in insects selected from the class Lepidoptera comprising *Spilarctia obliqua, Spodoptera litura* and *Heliothis armigera.*

13. A process as claimed in claim 5 wherein the concentration of the plant extract is about 2.5 mg/ml and the concentration of δ-endotoxin is about LC 5 or more of both the constituents.

14. A method of application of the insecticidal composition as claimed in claim 1 said method comprising the step of spraying the insecticidal composition on standing crops.

* * * * *

UNITED STATES PATENT AND TRADEMARK OFFICE
CERTIFICATE OF CORRECTION

PATENT NO. : 6,455,079 B1
APPLICATION NO. : 09/923586
DATED : September 24, 2002
INVENTOR(S) : Suman Preet Singh Khanuja et al.

It is certified that error appears in the above-identified patent and that said Letters Patent is hereby corrected as shown below:

Column 1, line 53, after "protection", delete ".", and insert -- , --.

Column 2, line 54, "thirungiensis" should be -- thuringiensis --.

Column 3, line 47, after "leaf", insert -- , --.

Column 3, line 52, "occur" should be -- occurs --.

Column 3, line 55, delete "1".

Column 4, line 65, "front" should be -- from --.

Column 4, line 66, "stages" should be -- stage --.

Column 5, line 1, after "Powder", insert -- : --.

Column 5, line 6, "the" should be -- The --.

Column 5, line 13, "th4en" should be -- then --.

Column 5, line 35, after "Combination", insert -- : --.

Column 5, TABLE 4, before "LC", delete "+".

Column 5, line 54, after "20%", delete ".", and insert -- , --.

Column 5, line 65, "human" should be -- humans --.

UNITED STATES PATENT AND TRADEMARK OFFICE
CERTIFICATE OF CORRECTION

PATENT NO.       : 6,455,079 B1
APPLICATION NO.  : 09/923586
DATED            : September 24, 2002
INVENTOR(S)      : Suman Preet Singh Khanuja et al.

It is certified that error appears in the above-identified patent and that said Letters Patent is hereby corrected as shown below:

Column 6, line 5, after "turmeric,", "cotton," should be -- and cotton --.

Column 6, line 14, after "concentrations", delete ".", and insert -- , --.

Signed and Sealed this

First Day of April, 2008

JON W. DUDAS
*Director of the United States Patent and Trademark Office*